(12) United States Patent
Ohishi

(10) Patent No.: US 6,850,792 B2
(45) Date of Patent: Feb. 1, 2005

(54) CONTRAST MEDIUM INJECTOR AND DIAGNOSIS SYSTEM EQUIPPED WITH THE SAME

(75) Inventor: Satoru Ohishi, Otawara (JP)

(73) Assignee: Kabushiki Kaisha Toshiba, Tokyo (JP)

( * ) Notice: Subject to any disclaimer, the term of this patent is extended or adjusted under 35 U.S.C. 154(b) by 387 days.

(21) Appl. No.: 10/013,686

(22) Filed: Dec. 13, 2001

(65) Prior Publication Data

US 2002/0071521 A1 Jun. 13, 2002

(30) Foreign Application Priority Data

Dec. 13, 2000 (JP) ........................................ 2000-378961

(51) Int. Cl.$^7$ ................................................ A61B 5/05
(52) U.S. Cl. ...................................... 600/407; 600/458
(58) Field of Search ................................ 600/458, 420, 600/426; 424/9.5

(56) References Cited

U.S. PATENT DOCUMENTS

| | | | | |
|---|---|---|---|---|
| 4,006,736 A | * | 2/1977 | Kranys et al. ............... | 600/432 |
| 4,854,324 A | * | 8/1989 | Hirschman et al. .......... | 600/432 |
| 5,792,056 A | * | 8/1998 | Prince ......................... | 600/420 |
| 6,080,107 A | * | 6/2000 | Poland ........................ | 600/458 |
| 6,240,311 B1 | * | 5/2001 | Prince ......................... | 600/420 |
| 6,463,318 B2 | * | 10/2002 | Prince ......................... | 600/420 |
| 6,540,676 B2 | * | 4/2003 | Kamiyama ................... | 600/437 |
| 6,641,538 B2 | * | 11/2003 | Nakaya et al. ............... | 600/458 |

\* cited by examiner

*Primary Examiner*—Ali Imam
(74) *Attorney, Agent, or Firm*—Oblon, Spivak, McClelland, Maier & Neustadt, P.C.

(57) ABSTRACT

An examination program is selected based on an input of an examination method or a region to be inspected on the side of an diagnostic X-ray system, and contrast conditions suitable for contrast examination which is realized by the selected examination protocol are transmitted to a contrast medium injector through a network or the like. The contrast medium injector receives the transmitted contrast conditions and performs control regarding contrast medium dosage based on the contrast conditions.

9 Claims, 5 Drawing Sheets

CONTRAST MEDIUM INJECTOR AND DIAGNOSIS SYSTEM EQUIPPED WITH THE SAME

CROSS-REFERENCE TO RELATED APPLICATIONS

This application is based upon and claims the benefit of priority from the prior Japanese Patent Application No. 2000-378961, filed Dec. 13, 2000, the entire contents of which are incorporated herein by reference.

BACKGROUND OF THE INVENTION

1. Field of the Invention

The present invention relates to a contrast medium injector, and a diagnosis system equipped with the same.

2. Description of the Related Art

A medical diagnosis system is designed to provide much information regarding an object based on an image and the like, and plays an important role in many medical practices including a disease diagnosis, a treatment, an operation plan, etc. Currently available medial diagnosis devices are mainly an ultrasonic diagnosis system, an X-ray CT scanner, an diagnostic X-ray system, a magnetic resonance imaging (MRI) system, a nuclear medical diagnosis system, and so on.

For diagnoses carried out by using such medial diagnosis systems, there is an examination method using a contrast medium. According to this contrast medium examination method, for example, in the case of photographing an X-ray image, a contrast medium having a large X-ray attenuation rate is used, and an internal or peripheral portion of an organ is extracted based on a shadow. A type or a dosage of a contrast medium used to photograph such an X-ray image varies depending on the purpose of the examination, and a region to be inspected.

Such a contrast medium is injected into the blood vessel, the intestine or the like of the object by, for example, a contrast medium injector. The contrast medium injector injects the contrast medium into the object by using power of a pneumatic pressure, a motor, a hydraulic pressure, etc. based on a dosage of the contrast medium and an injection pressure which are decided according to essential items, entered by an operator, including the purpose of the examination, the region to be inspected, and so on.

However, in the conventional contrast examination, the dosage of the contrast medium, the injection pressure, etc. must all be entered on the contrast device side for each examination. Consequently, the operator is required to carry out the burdensome operation of setting contrast medium conditions for each examination, which is one cause of the increase in burdens imposed on the operator and a work/examination time.

The present invention has been developed in view of the foregoing situations, and an object of the present invention is to provide a contrast medium injector capable of reducing burdens imposed on the operator and shortening an examination time by simplifying a method of setting contrast conditions. Another object of the present invention is to provide a diagnosis system equipped with the above contrast medium injector.

BRIEF SUMMARY OF THE INVENTION

In order to achieve the foregoing objects, the present invention takes the following means.

A first aspect of the present invention is a diagnosis system comprises: a contrast medium injector; a medical diagnosis system connected to the contrast medium injector; an input device configured to enter examination information; a memory configured to store a plurality of contrast conditions correlated with the examination information; and controller configured to read out, from the memory, a contrast condition correlated with the examination information entered from the input device and to control regarding contrast medium injection in the contrast medium injector based on the contrast conditions.

A second aspect of the present invention is a diagnosis system comprises: a contrast medium injector; and a medical diagnosis system connected to the contrast medium injector; wherein the medical diagnosis system comprising: an input device configured to enter examination information; a memory configured to store a plurality of contrast conditions correlated with the examination information; and a first controller configured to read out, from the memory, a contrast condition correlated with the examination information entered from the input device and to transmit the contrast condition to the contrast medium injector through a communication line; and the contrast medium injector comprising: a second controller configured to receive a contrast condition transmitted by the first controller and to control regarding contrast medium dosage based on the received contrast condition.

A third aspect of the present invention is a contrast medium injector comprises: a receiving device configured to receive a contrast condition from a medical diagnosis system through a communication line, and a controller configured to control regarding contrast medium injection based on the received contrast condition.

A fourth aspect of the present invention is a contrast medium injector comprises: a memory configured store a plurality of contrast conditions; a selecting device configured to select a contrast condition by an operator; and a controller configured to read out the selected contrast condition from the memory and to control regarding contrast medium injection based on the selected contrast condition.

According to the configuration described above, the method of setting contrast conditions can be simplified. As a result, it is possible to provide a contrast medium injector capable of reducing a burden imposed on an operator and shortening an examination time, and a diagnosis system equipped with the contrast medium injector.

DETAILED DESCRIPTION OF THE INVENTION

Next, description will be made of the first to third embodiments of the present invention with reference to the accompanying drawings. Hereinafter, components having similar functions and configurations will be denoted by similar reference numerals, and overlapped explanation will be made only when necessary.

(First Embodiment)

First, description will be made of the configurations of a contrast medium injector and a diagnosis system equipped with the contrast medium injector according to the first embodiment of the present embodiment by referring to FIG. 1. To make explanation specific, it is assumed that medical equipment constituting the diagnosis system is an diagnostic X-ray system.

Figure 1:
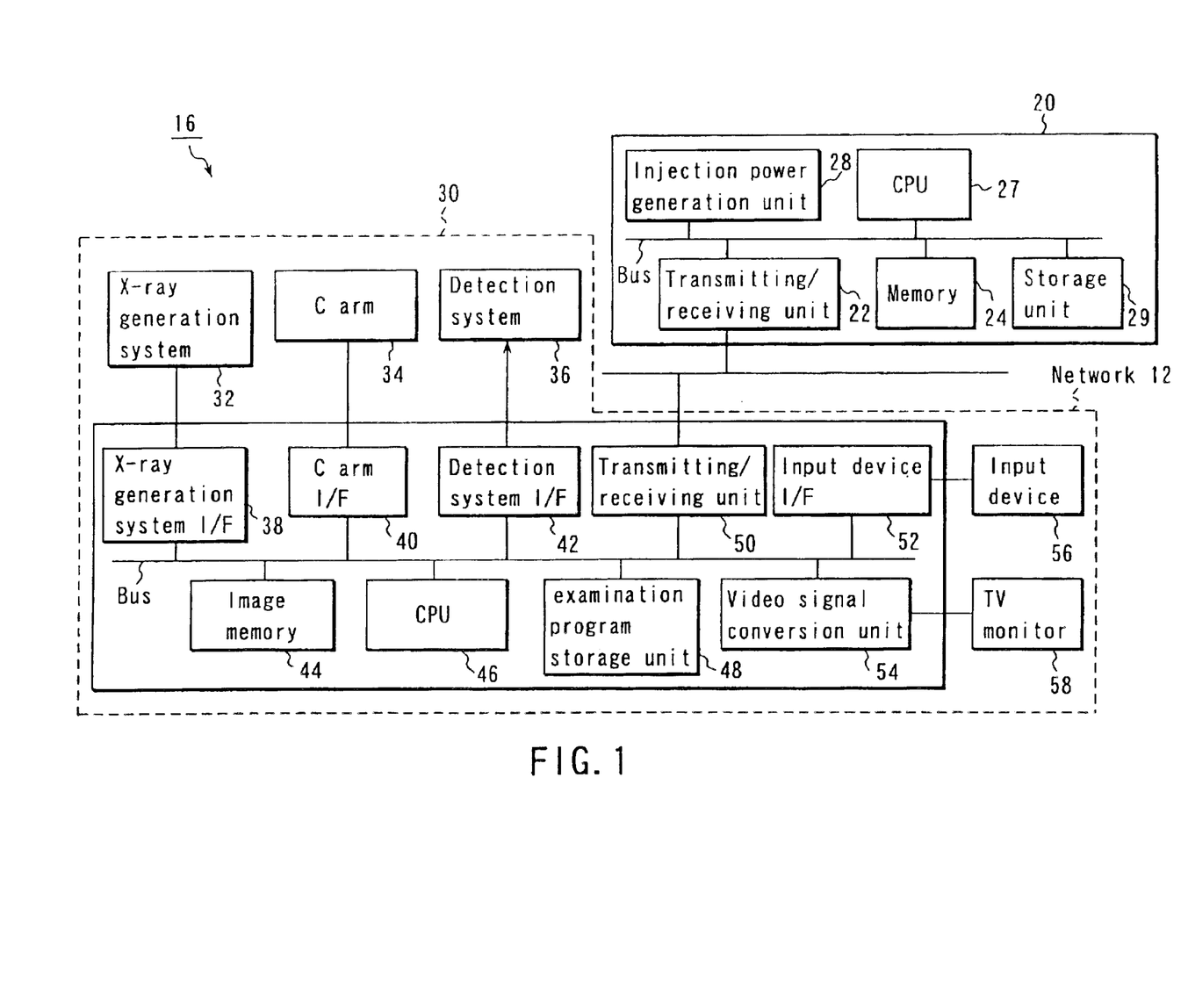
FIG. 1 shows a schematic configuration view showing a contrast medium injector 20 and a diagnosis system 10 according to a first embodiment of the present invention.

FIG. 1 schematically shows the configurations of a contrast medium injector 20 and a diagnosis system 10 according to the embodiment.

The diagnosis system 10 comprises the contrast medium injector 20, an diagnostic X-ray system 30, and a network 12 which interconnects the contrast medium injector 20 and the diagnostic X-ray system 30. Hereinafter, each component will be described.

(Diagnostic X-ray System)

The diagnostic X-ray system 30 includes an X-ray controller 32, a C arm 34, an X-ray detection system 36, an X-ray generation system I/F 38, a C arm I/F 40, a detector I/F 42, an image memory 44, a CPU 46, an examination program storage unit 48, a transmitting/receiving unit 50, an input device I/F 52, a video signal conversion unit 54, an input device 56, and a TV monitor 58.

The X-ray generation system 32 includes a high voltage generator, an X-ray tube, and an X-ray diaphragm, which are not shown. The high voltage generator supplies a high voltage to the X-ray tube. The X-ray tube is a vacuum tube which generates X rays. This X-ray tube specifically generates X rays by accelerating electrons with the high voltage applied from the high voltage generator, and clashes the electrons on a target. The generated X rays are radiated to an object. The X-ray diaphragm is provided between the X-ray tube 121 and the object, and adapted to diaphragm an X-ray beam radiated from the X-ray focus of the X-ray tube to a desired received image size.

The C arm 34 is a holder for the C-shaped X-ray generation system and the X-ray detection system. This C arm 34 includes the X-ray tube or the like provide in one end, and the X-ray detector provided in the other end, both of which are disposed to face each other via the object, and fixed and held. The C arm is capable of sliding and obtaining an X-ray image at an optional angle of optical axis.

The detection system 36 includes an X-ray plane detector which is relatively thin, and planar in a detection surface, or an imaging intensifier (I. I), an optical system, etc. The X-ray plane detector generates an electron hole by irradiating a photoelectric layer with X rays passed through the object, stores this electron hole by a semiconductor switch, and then detects an X-ray signal by reading it out as an electric signal. The I. I converts the information of X-rays passed through the object into optical information on a fluorescent screen, and then clashes a photoelectron generated based on the optical information on an output fluorescent screen to generate a high-intensity optical image.

The X-ray photographing system I/F 38 is an interface provided to transfer a control signal issued from the CPU 46 to generate X rays to the X-ray photographing system 32.

The C arm I/F 40 is an interface provided to transfer a control signal issued from the CPU 40 to drive the C arm 34 to a not-shown C arm drive unit.

The detection system 1/F 42 receives transparent image data entered from the detection system 36, and transfers the data to the CPU 46, the image memory 44, or the like. The detection system I/F 42 is also an interface provided to transfer a control signal from the CPU to the detection system 36.

The image memory 44 is a storage unit provided to receive the digital transparent image data entered from the detection system I/F 42, and store a plurality of X-ray diagnosis image data photographed for every frames or separately photographed.

The CPU 46 is a central processing unit provided to perform control regarding the collection of X-ray transparent image data, and the image processing of the collected image data. Also, among a plurality of examination programs stored in the examination program storage unit 48, the CPU 46 selects an examination program regarding an examination method or a region to be inspected, which is entered from the input device 56. Then, the CPU 46 transfers the selected examination program through the transmitting/receiving unit 50 to the contrast medium injector 20. Detailed description will be made later of the selecting operation of the examination program.

The examination program storage unit 48 is provided to store a plurality of examination programs. Here, "examination program" defines the content of contrast medium examination, for example, a region to be inspected, a method for the examination, and a procedure for the examination. Thus, once an examination program is decided, a total dosage of the contrast medium, a dosage of contrast medium per unit time, etc., are decided to realize the examination program. Hereinafter, conditions for deciding a total dosage or contrast time, and a dosage per unit time of a predetermined contrast medium will be defined as contrast conditions. Accordingly, for example, since a dosage per unit time can be decided even with an injection speed, a rise time at injection (pressure), etc., these contents are also included in the contrast conditions.

In addition, contrast conditions corresponding to each examination program are set values for contrast conditions displayed on the setting screen of the examination program, or set values on the setting window of the contrast conditions to be called from the screen. It is assumed that the set value is correlated to the examination program, and stored in the storage unit 48. When the set value is changed on the setting screen or the like of each examination program, this change is naturally reflected in the contrast conditions stored in correlation with the examination program.

The transmitting/receiving unit 50 is transfer means provided, as described later, to transfer the contrast conditions selected according to the examination method or the region to be inspected, and a signal for permitting/inhibiting the injection of contrast medium through the network to the contrast medium injector. The transmitting/receiving unit 50 also receives confirmation information entered from the contrast medium injector to confirm the contrast conditions. Preferably, the transmitting/receiving of such information should be executed in real time.

The input device I/F 52 converts an input signal from the input device 56 into a bit string, and transfers it to each control unit or the like.

The video signal conversion unit 54 converts a signal string of the entered X-ray transparent image data into a raster signal string of a video format.

The input device 56 includes a keyboard, various switches, a mouse, etc., and it is used when an image is selected or later-described position information is entered.

The TV monitor 58 displays the reconstructed transparent image data generated by the video signal conversion unit 32.

(Contrast Medium Injector)

The contrast medium injector 20 includes a receiving unit 22, a memory 24, a CPU 27, an injection power generation unit 28, and a storage unit 29.

The transmitting/receiving unit 22 is a device provided to receive an examination program for setting predetermined contrast conditions, which has been transferred through the network from the transmitting/receiving unit 50. The transmitting/receiving unit 22 also sends confirmation information for confirming the received contrast conditions to the diagnostic X-ray system 39.

The memory 24 is storage means for temporarily storing the examination program received by the receiving unit 22.

The CPU 27 controls the injection pressure generation unit 28 based on the received examination program so as to execute contrast medium injection under predetermined contrast conditions.

The injection power generation unit 28 generates power for injecting a contrast medium into the object under the predetermined contrast conditions (a dosage, an injection pressure, and the like), based on control by the CPU 27. Specifically, the contrast conditions received from the diagnostic X-ray system 30 are reflected in a control parameter regarding the injection power generation unit 28, and contrast medium injection is realized according to the contrast conditions.

As a general power source, one may be selected from a pneumatic pressure, a motor, a hydraulic pressure, etc.

The storage unit 29 is nonvolatile storage means provided to store the received examination program regarding the examination method or each region to be inspected.

(Network)

The network 12 is a communication network based on an electric line for connecting the diagnostic X-ray system 30, the contrast medium injector 20 or other medical equipment. Through the network 12, communications can be carried out irrespective of wire or wireless. For example, wire communications or the like can be carried out by RS-232C, and wireless communications or the like by infrared rays.

(Contrast Medium Injecting Operation)

Figure 2:
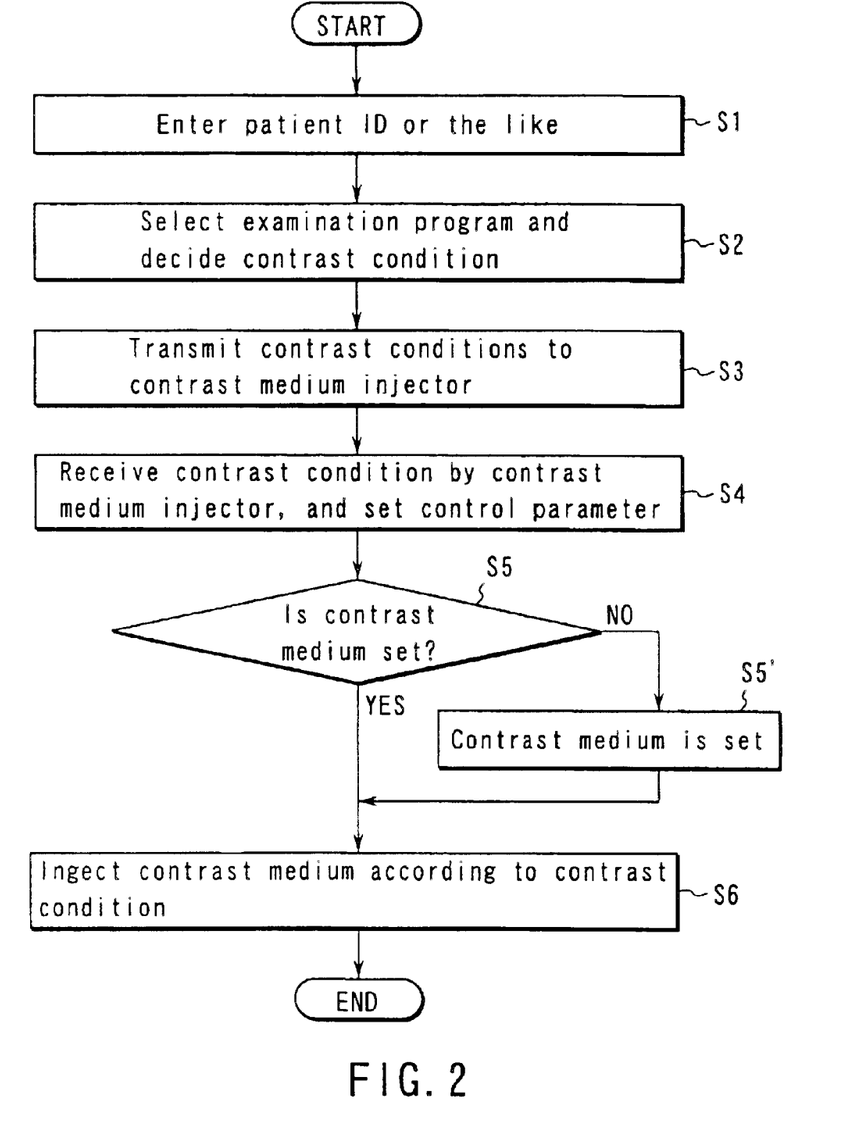
FIG. 2 is a flowchart showing a processing procedure of contrast medium injection which is carried out by the diagnosis system 10.

FIG. 2 is a flowchart showing the process of injecting a contrast medium, which is executed by the diagnosis system 10. Now, the contrast medium injection of the diagnosis system 10 will be described by referring to FIGS. 1 and 2.

According to the diagnosis system 10 of the embodiment, it is possible to set desired contrast conditions in the contrast medium injector only by entering an examination method or a region to be inspected on the diagnostic X-ray system side. Specifically, the entry of the examination method or the region to be inspected causes an examination program to be automatically decided, which is used to set contrast conditions corresponding to the examination method or the region to be inspected in the contrast medium injector. Then, on the contrast medium injector side, contrast conditions are set based on the received examination program, and contrast medium injection is executed.

A specific process is as follows.

In FIG. 2, first, as processing before diagnosis, a patient ID, an examination method, a region to be inspected or the like is entered from the input device 56 by an operator (step S1).

Subsequently, based on the entered examination method, or the region to be inspected, an examination program to be used for the examination is selected from the storage unit 48. Contrast conditions are also decided based on the examination program (step S2).

The contrast condition defines, for example, an injection speed, a dosage, a rise time at injection, or the like simultaneously with the selection of the examination program. The decided contrast condition is sent from the transmitting/receiving unit 50 of the diagnostic X-ray system 30 to the transmitting/receiving unit 22 of the contrast medium injector 20 (step S3).

On the contrast medium injector 20 side, the condition is received by the transmitting/receiving unit 22, and temporarily stored in the memory 24. Further, the CPU 27 sets a control parameter for the injection power generation unit 28 based on the condition (step S4).

Subsequently, determination is made as to the setting of a contrast medium in a not-shown injector (step S5). In this case, if the setting of the contrast medium is determined, the contrast medium is injected according to the contrast conditions, and examination is started (step S6). On the other hand, if no setting of the contrast medium is determined, then after the contrast medium is set (step S5'), the contrast medium is injected according to the contrast conditions, and examination is started (step S6).

Preferably, the transferred contrast conditions should be stored in the storage unit 29 in correlation with the examination program. With this configuration, if one and the same examination program is selected again on the diagnostic X-ray system 30 side, only information specifying contrast conditions corresponding to the examination program is sent to the contrast medium injector 20, accordingly enabling the same operation to be realized.

(Second Embodiment)

A contrast medium injector according to the second embodiment is designed to set desired contrast conditions only at the contrast medium injector. Thus, the contrast medium injector of the embodiment comprises input means for entering contrast conditions, and executes contrast medium injection according to the contract condition entered by the input means.

Figure 3:
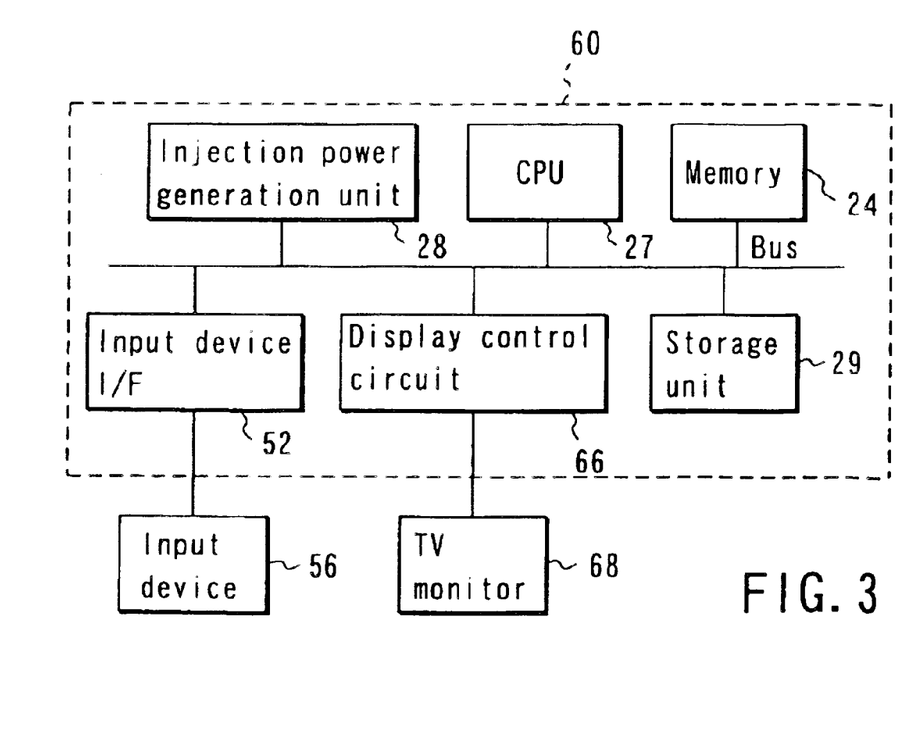
FIG. 3 shows a schematic configuration view of a contrast medium injector 60 according to a second embodiment.

FIG. 3 schematically shows the configuration of a contrast medium injector 60 according to the second embodiment. Components similar to those of the contrast medium injector 20 shown in FIG. 1 are denoted by similar reference numerals, and description thereof will be omitted.

In FIG. 3, the contrast medium injector 60 further comprises an input device 56, an input device I/F 52, a TV monitor 68, and a display control circuit 66.

The TV monitor 68 is display means provided to display a setting screen of contrast conditions, and the display control circuit 66 performs control regarding displaying.

Next, description will be made of a contrast medium injection operation carried out by the contrast medium injector 60 by referring to FIGS. 3 and 4.

Figure 4:
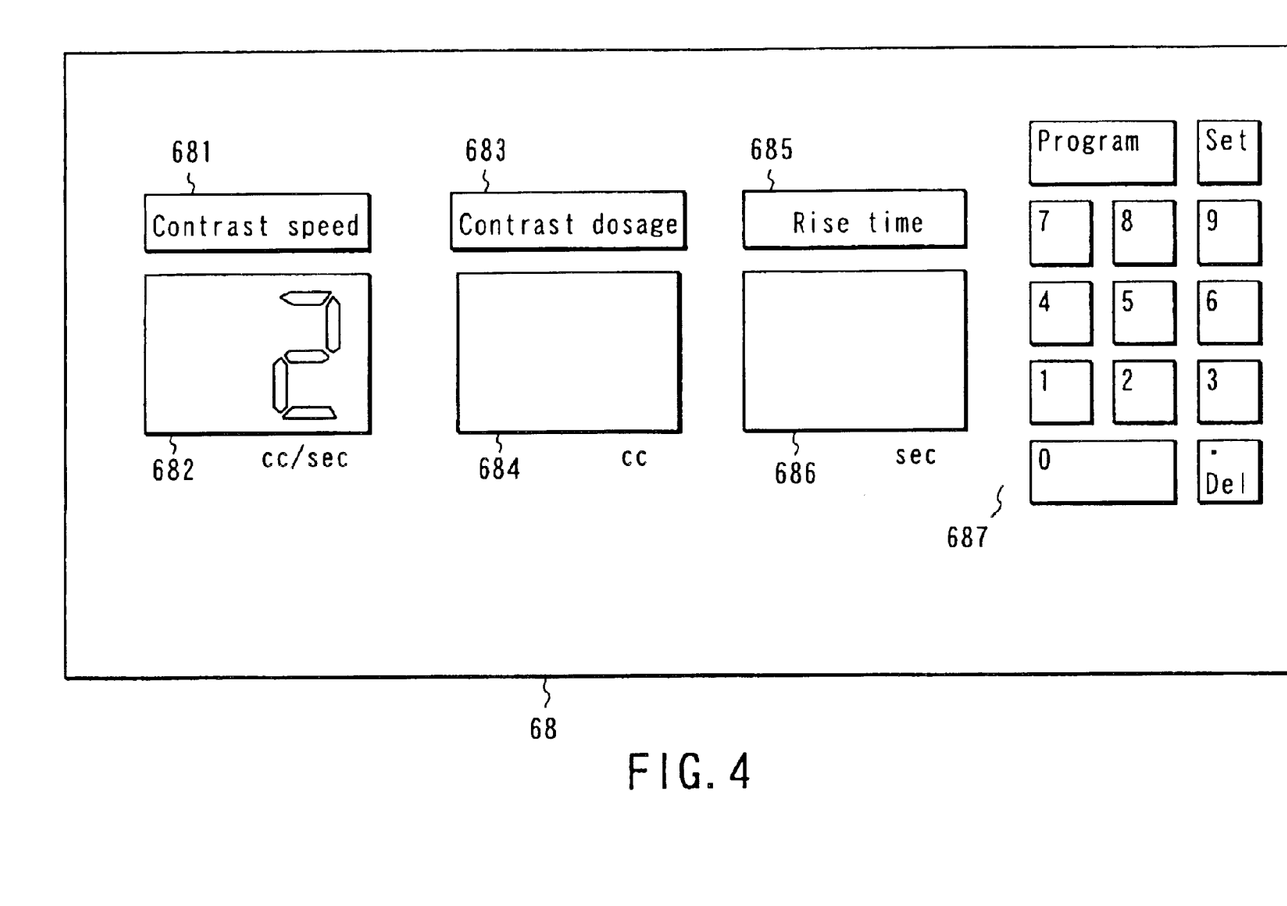
FIG. 4 is a view showing a setting screen of contrast conditions which is displayed on a TV monitor 68 by a predetermined operation.

FIG. 4 shows the setting screen of contrast conditions, which is displayed on the V monitor 68 by a predetermined operation. The screen shown displays a contrast speed button 681, etc., and a ten key 687.

In FIG. 4, for example, to set a contrast speed, the contrast speed button 681 is first pressed. This operation enables a contrast speed to be set. If a desired contrast speed is, for example, 2 cc/sec., the key "2" of the ten key 687 is clicked by the input device 56, and then the key "set" of the ten key 687 is pressed, thus setting the contrast speed of 2 cc/sec. Other set values, i.e., "contrast dosage", and "rise time", can be set by similar operations.

The content of the contrast conditions set in the foregoing manner is displayed similarly to the display below the contrast button 681 shown in FIG. 4.

Next, description will be made of the operation of storing contrast conditions set in the foregoing manner as a program in the storage unit 29.

After the setting of the contrast conditions, a PROGRAM button in the ten key 687 is first pressed. This operation enables the set current contrast conditions to be stored as a program.

Then, for example, a 2-digit numeral as ID specifying the program is pressed by using the ten key, and then the content of the current contrast conditions can be stored in the storage unit 29 by pressing a Store button in the ten key 687.

To reuse the contrast conditions thus stored, first the PROGRAM button is pressed, and then after the 2-digit numeral specifying the program is pressed, a Set button is pressed. By such a series of operations, the contrast conditions stored in the storage unit 29 are read out, enabling a corresponding value to be set. Accordingly, the time and labor of entering each set value of contrast conditions for each examination can be omitted.

Especially, the automatic setting of contrast conditions realized in the first embodiment necessitates both of the medial equipment and the contrast medium injector to be reconstructed. On the other hand, the automatic setting of the contrast conditions of the second embodiment necessitates only the contrast medium injector to be reconstructed. Therefore, development is relatively easier, and development costs and device expenses can be reduced.

(Third Embodiment)

A contrast medium injector or a diagnosis system according to the third embodiment is different from the ones of the first and second embodiments in that a confirmation function is provided to enable an operator to confirm contrast conditions to be set. This confirmation function assures examination/diagnosis work more. Hereinafter, description will be made of respective cases where the third embodiment is applied to the contrast medium injectors 20 and 60 of the first and second embodiments.

For example, it is assumed that contrast conditions corresponding to a selected examination program in the contrast medium injector 20 are displayed on the display of the medical equipment (the diagnostic X-ray 30) or the contrast medium injector 20, and photographing is not permitted unless the confirmation button is pressed in this state.

With such a configuration, the operator can visually confirm the content of contrast conditions to be set, and thus examination/diagnosis work can be assured more.

In addition, for example, it is assumed that the content of contrast conditions corresponding to a program called based on an ID number in the contrast medium injector 60 is temporarily stored in the monitor 58 or 68, and photographing is not permitted unless the confirmation button is pressed again.

With such a configuration, a similar advantage can be obtained by the contrast medium injector 60 or the diagnosis system.

In any of the devices of the first and second embodiments, if there is a difference in set values at the time of confirmation, by repeating the existing operation according to each embodiment again, it is possible to update contrast conditions to be set.

(Fourth Embodiment)

A diagnosis system according to the fourth embodiment has a function provided in the communication system to confirm contrast conditions set in the contrast medium injector 20. In other words, contrast medium injection is carried out according to a handshaking type protocol, and the contrast injection is executed only when an agreement is reached between the contrast medium injector 20 and the diagnostic X-ray system 30. This confirmation function can prevent any operation mistakes. In addition, if used together with the artificial confirmation function described above with reference to the third embodiment, examination/diagnosis work can be carried out more surely.

Figure 5:
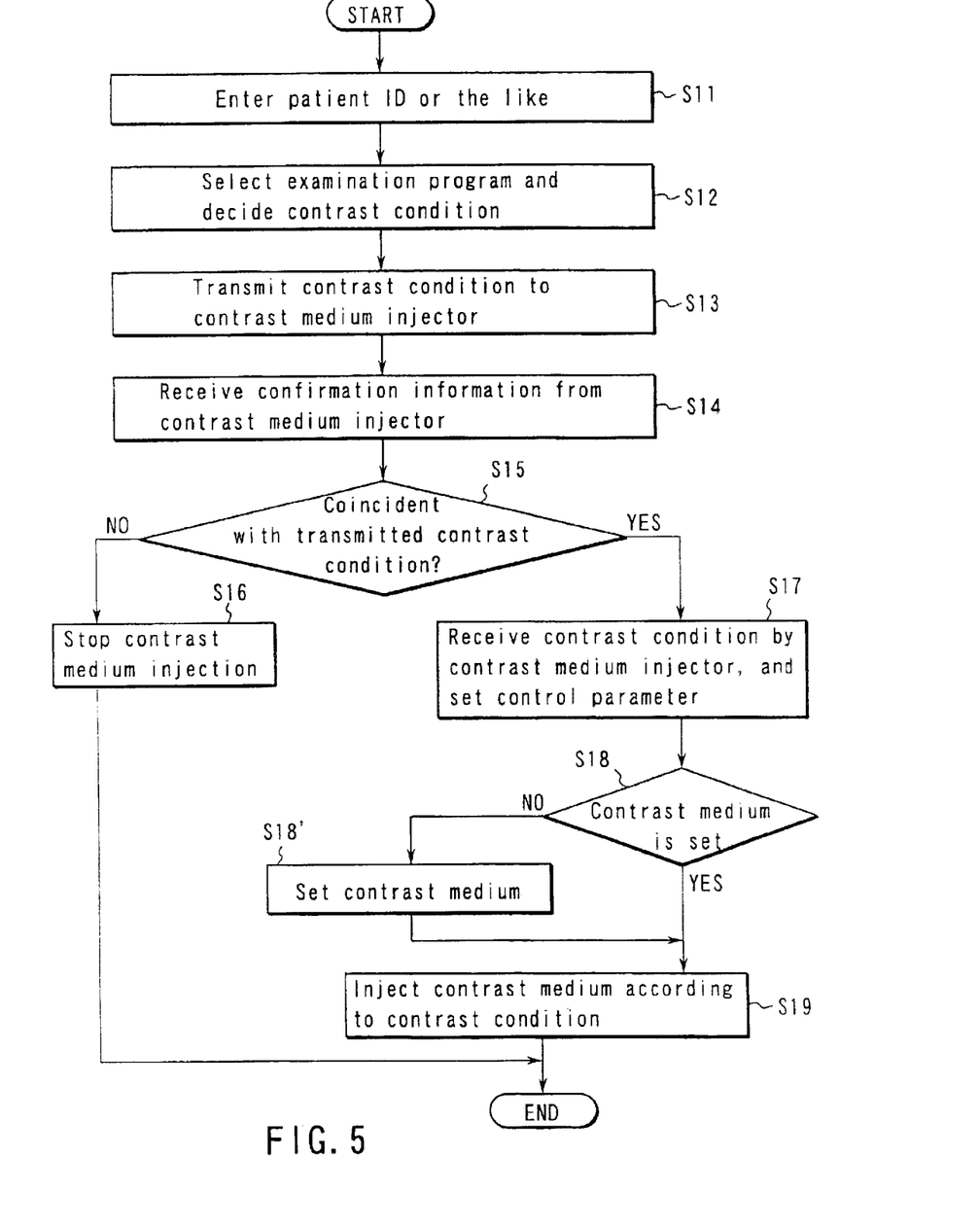
FIG. 5 is a flowchart showing a processing procedure of contrast medium injection which is carried out by a diagnosis system 10 of a fourth embodiment.

FIG. 5 is a flowchart showing the process of contrast medium injection, which is carried out by the diagnosis system 10 of the fourth embodiment.

In FIG. 5, first, as processing before diagnosis, a patient ID or the like is entered from the input device 56 by an operator (step S11). Subsequently, based on the entered examination method or the like, an examination program to be used for the examination is selected from the storage unit 48. Contrast conditions are also decided based on this selected examination program (step S12). The decided contrast conditions are sent from the transmitting/receiving unit 50 of the diagnostic X-ray system 30 to the transmitting/receiving unit 22 of the contrast medium injector 20 (step S13).

On the contrast medium injector 20 side, each condition is received by the transmitting/receiving unit 22, and temporarily stored in the memory 24. Further, the CPU 27 sends the confirmation information of the received contrast conditions to the diagnostic X-ray system 30 by the transmitting/receiving unit 22, and the diagnostic X-ray system 30 receives the confirmation information by the transmitting/receiving unit 50 (step S14). Here, the confirmation information of the received contrast conditions indicates the nature of the contrast conditions received by the contrast medium injector.

Subsequently, the CPU 46 of the diagnostic X-ray system 10 makes determination as to the coincidence of contrast information generated by the diagnostic X-ray system 10 with contrast information received by the contrast medium injector (step S15).

If non-coincidence is determined in step S15, the CPU 46 sends a signal indicating the stoppage of contrast medium injection to the contrast medium injector 20. The CPU 27 of the contrast medium injector 20 stops the contrast medium injection in response to the stoppage signal received by the transmitting/receiving unit 22 (step S16).

On the other hand, if coincidence is determined in step S15, then the CPU 46 of the diagnostic X-ray system 30 sends a signal permitting the execution of contrast medium injection to the contrast medium injector 20. The CPU 27 of the contrast medium injector 20 sets a control parameter for the injection power generation unit 28 based on the received contrast conditions, in response to the permission signal received by the transmitting/receiving unit 22 (step S17).

Subsequently, determination is made as to the setting of a contrast medium in a not-shown injector (step S18). In this case, if the setting of the contrast medium is determined, the contrast medium is injected according to the contrast conditions, and examination is started (step S19). On the other hand, if no setting of the contrast medium is determined, then after the contrast medium is set (step S18'), the contrast medium is injected according to the contrast conditions, and examination is started (step S19).

With this configuration, the content of a contrast to be set can be confirmed at the communication system, and examination/diagnosis work can be carried out more surely.

The foregoing configuration provides the following advantages.

A predetermined examination program is selected by entering an examination method, a region to be inspected or the like at the medical diagnosis device, and contrast conditions beforehand stored in the examination program are automatically transferred to the contrast medium injector. On the contrast medium injector side, the received contrast conditions are set, and contrast medium injection is executed based on the contrast conditions.

Therefore, the setting of the contrast conditions can be facilitated. As a result, it is possible to provide the contrast medium injector capable of reducing a burden imposed on the operator, and shortening examination time, and the diagnosis system equipped with the same.

Especially, if an object is an adult, and a condition is stable to a certain extent, since contrast conditions are usually set by an examination program, the foregoing configuration enables proper contrast examination to be executed, thus making it possible to shorten examination time.

The preferred embodiments of the present invention have been described. However, as obvious to those skilled in the art, various modifications and changes can be made within the teachings of the present invention. It is therefore understood that such modifications and changes made fall within the scope of the present invention. For example, as described below, various modifications can be made without departing from the teaching of the present invention.

(1) In the third embodiment, the contrast medium injector was designed to enable the operator to visually confirm contrast conditions. However, the contrast conditions may be notified by voice to the operator.

With such a configuration, easy confirmation can be made aurally, further assuring examination/diagnosis work.

(2) Apparently, each of the foregoing contrast medium injectors can manually set contrast conditions. Thus, for example, in the confirmation of the contrast conditions described above with reference to the third embodiment, if a set value is different from a desired value, then the operator can manually make adjustment and carrying resetting.

With such a configuration, if the set value of the contrast medium is different from a desired value, it is not necessary to carry out re-execution from the entry of the region to be inspected or the like, hence improving workability.

The present invention is not limited to the foregoing embodiments, and various modifications can be made without departing from the teachings of the present invention. The embodiments can be properly combined when permitted, and the advantages of combination can be provided. Further, the embodiments include the inventions of various stages, and various inventions can be extracted by the proper combination of a plurality of disclosed components. For example, even if some of all the components of the embodiments are omitted, the problems described above in the background of the present invention can be solved and, when at least one of the foregoing advantages of the present invention is obtained, the configuration with the component omitted can be extracted as an invention.

As apparent from the foregoing, according to the present invention, the method of setting contrast conditions can be simplified. As a result, it is possible to provide a contrast medium injector capable of reducing a burden imposed on the operator, and shortening examination time, and a diagnosis system equipped with same.

What is claimed is:

1. A diagnosis system comprising:
   a contrast medium injector;
   a medical diagnosis system connected to the contrast medium injector;
   an input device configured to enter examination information;
   a memory configured to store a plurality of contrast conditions correlated with the examination information; and
   controller configured to read out, from the memory, a contrast condition correlated with the examination information entered from the input device and to control a contrast medium injection in the contrast medium injector based on the contrast condition read out from the memory.

2. The diagnosis system according to claim 1, wherein the contrast condition includes at least one of a total dosage of the contrast medium, an injection time, a contrast medium injection speed per unit time, a rise time at contrast medium injection, and a contrast medium injection pressure.

3. The diagnosis system according to claim 2, wherein the controller controls the contrast medium injection based on the contrast condition read out from the memory, only when a predetermined input operation is carried out by the operator.

4. The diagnosis system according to claim 1, wherein the examination information includes at least one of an examination method and a region to be inspected.

5. The diagnosis system according to claim 4, wherein the controller controls the contrast medium injection based on the contrast condition read out from the memory, only when a predetermined input operation is carried out by the operator.

6. The diagnosis system according to claim 1, wherein the controller controls the contrast medium injection based on the contrast condition read out from the memory, only when a predetermined input operation is carried out by the operator.

7. A diagnosis system comprising:
   a contrast medium injector; and
   a medical diagnosis system connected to said contrast medium injector;
   wherein said medical diagnosis system comprises:
      an input device configured to enter examination information;
      a memory configured to store a plurality of contrast conditions correlated with the examination information; and
      a first controller configured to read out, from the memory, a contrast condition correlated with the examination information entered from the input device and to transmit the contrast condition to said contrast medium injector through a communication line; and
   said contrast medium injector comprising:
      a second controller configured to receive the contrast condition transmitted from said first controller and to control a contrast medium dosage based on the received contrast condition.

8. The diagnosis system according to claim 7, wherein said second controller transmits information to identify the received contrast condition to said medical diagnostic system and excites a contrast medium injection only when said second controller receives information of correspondence between the transmitted contrast condition and the received contrast condition from said medical diagnosis system.

9. The diagnosis system according to claim 7, wherein said first controller transmits confirmation information to permit a contrast medium injection to said contrast medium injector when a predetermined input operation is carried out by the operator; and
   said second controller executes the contrast medium injection only when said second controller receives the confirmation information.

* * * * *